United States Patent [19]

Collins

[11] Patent Number: 5,567,433
[45] Date of Patent: Oct. 22, 1996

[54] LIPOSOME PREPARATION AND MATERIAL ENCAPSULATION METHOD

[75] Inventor: David Collins, Thousand Oaks, Calif.

[73] Assignee: Amgen Inc., Thousand Oaks, Calif.

[21] Appl. No.: 381,613

[22] Filed: Jan. 30, 1995

Related U.S. Application Data

[62] Division of Ser. No. 148,099, Nov. 5, 1993, abandoned.

[51] Int. Cl.$^6$ ............................ A61K 9/127; B01J 13/02
[52] U.S. Cl. ............................ 424/450; 264/4.1; 264/4.3
[58] Field of Search ............................ 424/450; 264/4.1, 264/4.3

[56] References Cited

U.S. PATENT DOCUMENTS

| | | | |
|---|---|---|---|
| 4,229,360 | 10/1980 | Schneider et al. | 260/403 |
| 4,241,046 | 12/1980 | Papahadjopoulos | 424/450 |
| 4,311,712 | 1/1982 | Evans et al. | 424/365 |
| 4,515,736 | 5/1985 | Deamer | 264/4.3 |
| 4,857,319 | 8/1989 | Crowe et al. | 424/94.1 |
| 5,077,056 | 12/1991 | Bally et al. | 424/450 |
| 5,104,661 | 4/1992 | Lau | 424/450 |

FOREIGN PATENT DOCUMENTS

| | | |
|---|---|---|
| 0172007 | 5/1991 | European Pat. Off. . |
| 57-82311 | 5/1982 | Japan . |
| 2002319 | 2/1979 | United Kingdom . |

OTHER PUBLICATIONS

"Solute Distributions and Trapping Efficiencies Observed In Freeze-Thawed Multilamellar Vesicles" by Mayer et al., *Biochimica et Biophysica Actta*; vol. 817 (1985) pp. 193-196.

"Dehydration-Rehydration Vesicles: A Simple Method For High Yield Drug Entrapment In Liposomes" by Kirby et al., *Bio/Technology*; (Nov. 1984) pp. 979-984.

"The Application Of Liposomes To Cosmetics" by Suzuki and Sakon, *Cosmetics & Toiletries*; vol. 105 (1990) pp. 65-78.

"Liposome-Encapsulated Hemoglobin As A Red Cell Surrogate" by Beissinger et al., *Trans Am Soc Artif Intern Organs*; vol. XXXII (1986) pp. 58-63.

"Topical Liposomes-An Update and Review Of Uses And Production Methods" by Siciliano, *Cosmetics & Toiletries*; vol. 100 (1985) pp. 43-46.

"Liposomes With A Large Trapping Capacity Prepared by Freezing And Thawing Of Sonicated Phospholipid Mixtures" by Pick, *Archives of Biochemistry and Biophysics*; vol. 212, No. 1 (1981) pp. 186-194.

Primary Examiner—Gollamudi S. Kishore
Attorney, Agent, or Firm—Daniel R. Curry

[57] ABSTRACT

The present invention relates to a method of producing liposomes useful for encapsulating and delivering a wide variety of biologically active materials. The invention provides liposomes and a production method which is simple, feasible and inexpensive for the large-scale commercial manufacturing of liposomes and encapsulated materials. The method involves the formation of a liposome dispersion in the absence of an organic solvent or detergent, one or several cycles of freezing and thawing the liposomes, and dehydration of the liposome dispersion to form a lipid powder. When desired, the lipid powder is hydrated in the presence of the biologically active material whereby the material is encapsulated in reconstituted liposomes. The method can also include combining the liposome dispersion with a bulking agent prior to the dehydration and formation of the lipid powder. The addition of the bulking agent facilitates the handling of the lipid powder as well as its rapid dispersal upon hydration.

6 Claims, 5 Drawing Sheets

LIPOSOME PREPARATION AND MATERIAL ENCAPSULATION METHOD

This application is a division of U.S. Ser. No. 08/148,099, filed Nov. 5, 1993, now abandoned.

BACKGROUND OF THE INVENTION

1. Field of the Invention

The present invention relates generally to liposomes, and more particularly to a method of producing liposomes useful for encapsulating biologically active materials. The liposomes are, therefore, useful in applications such as in vivo drug delivery and gene therapy and as diagnostic agents.

2. Description of the Background

Liposomes are microscopic vesicles, generally spherically shaped, formed from one or more lipid walls. The walls are prepared from lipid molecules, which have the tendency both to form bilayers and to minimize their surface area. The lipid molecules that make up a liposome have hydrophilic and lipophilic portions. Upon exposure to water, the lipid molecules form a bilayer membrane wherein the lipid ends of the molecules in each layer are directed to the center of the membrane, and the opposing polar ends form the respective inner and outer surfaces of the bilayer membrane. Thus, each side of the membrane presents a hydrophilic surface while the interior of the membrane comprises a lipophilic medium.

Liposomes can be classified into several categories based on their overall size and the nature of the lamellar structure. The classifications include small unilamellar vesicles (SUV), multilamellar vesicles (MLV), large unilamellar vesicles (LUV), and oligolamellar vesicles. SUVs range in diameter from approximately twenty to fifty nanometers and consist of a single lipid bilayer surrounding an aqueous compartment. A characteristic of SUVs is that a large amount of the total lipid, about 70%, is located in the outer layer of the bilayer. The most frequently encountered and easily prepared liposomes are the multilamellar vesicles. Where SUVs are single compartment vesicles of a fairly uniform size, MLVs vary greatly in diameter up to about 30,000 nanometers and are multicompartmental in their structure wherein the liposome bilayers are typically organized as closed concentric lamellae with an aqueous layer separating each lamella from the next. Large unilamellar vesicles are so named because of their large diameter which ranges from about 600 nanometers to 30 microns. Oligolamellar vesicles are intermediate liposomes having a larger aqueous space than MLVs and a smaller aqueous space than LUVs. Oligolamellar vesicles have more than one internal compartment and possibly several concentric lamellae, but they have fewer lamellae than MLVs.

A variety of methods for preparing liposomes are known in the art, several of which are described in *Liposome Technology* (Gregoriadis, G., editor, three volumes, CRC Press, Boca Raton 1984) or have been described by Lichtenberg and Barenholz in *Methods of Biochemical Analysis*, Volume 33, 337–462 (1988). Liposomes are also well recognized as useful for encapsulating biologically active materials. Preparation methods particularly involving the encapsulation of DNA by liposomes, and methods that have a direct application to liposome-mediated transfection, have been described by Hug and Sleight in *Biochimica* and *Biophysica Acta*, 1097, 1–17 (1991).

When liposomes form, solvent and solute molecules become trapped in their lumen. The volume encapsulated, or capture volume, is dependent on the size of the liposomes, the lipid composition of the vesicles and the ionic composition of the medium. The fraction of the solvent entrapped by liposomes is defined as the encapsulation or entrapment efficiency and is proportional to both lipid concentration and vesicle radius. The fraction of solute sequestered inside the liposomes is generally directly proportional to the fraction of solvent entrapped.

Although the encapsulation of biologically active materials in liposomes has significant potential for delivering such materials to targeted sights in the human body, the production of encapsulated materials on a commercially feasible scale has been a problem. In order for liposomes to be used more widely for therapeutic purposes, it is desirable that the preparation process satisfy the following standards:
1) a high degree of encapsulation can be attained;
2) organic solvent or detergent can be completely removed from the final product or their use avoided;
3) the final product is obtainable by a simple procedure;
4) preparation can be carried out on a large scale;
5) the stability of the liposomes supports an appropriate storage period; and
6) the encapsulated material is not partially or completely denatured or inactivated during liposome production or encapsulation.

A method for preparing liposomes with a water-soluble, biologically active compound using lyophilization is disclosed in Evans U.S. Pat. No. 4,311,712 et. al. Evans, et. al., however, state that their methods are not particularly suitable for aqueous soluble materials. Moreover, the disclosed method of preparation requires the mixture of the biologically active material with an organic solvent. Felgner, et al. (EP 172 007 B) also describe a technique incorporating an organic solvent. One object of the present invention is to avoid the use of organic solvents or detergents in forming the liposomes because these substances are difficult to remove, present health hazards or interact unfavorably with the biologically active molecules to be encapsulated.

It is also known that liposomes and their contents may be relatively unstable in aqueous dispersion. Accordingly, an attempt to increase the relatively short storage life of certain liposomal products by dehydrating the dispersion has been the focus of several liposome preparation methods. For example, the aqueous dispersion of encapsulated material is lyophilized to form a stable powder which can be stored for a long period and from which, with an aqueous medium, a liposome dispersion can be reconstituted (see Schneider, et. al. in U.S. Pat. No. 4,229,360). U.S. Pat. No. 4,515,736 (D. Deamer) also describes an encapsulation method in which liposome dispersions are dried in the presence of the material to be encapsulated. As the solution is dried to a highly viscous concentrated mixture, the individual liposomes fuse to form multilamellar structures which capture the material to be encapsulated between the lipid lamellae. Upon rehydration, lipid vesicles form which encapsulate the material. Crowe, et al. (U.S. Pat. 4,857,319) describe a method for preserving liposomes involving freeze drying a mixture containing the lipid vesicles, the material to be encapsulated and a disaccharide preserving agent. Each of these methods requires that the biologically active material be subjected to the lyophilization procedure. In contrast, it is a further object of the present invention to encapsulate a material while avoiding the need to subject that material to such rigorous manipulations as lyophilization, thereby decreasing the possibility of physically inactivating or degrading the material to be encapsulated.

Mayer, et. al. (U.S. Pat. No. 5,077,056) describe a liposome preparation method involving the use of small ions to produce gradients which enhance the retention of charged biologically active agents, and optionally involving subjecting the liposome and biologically active agents to a freeze-thaw process during the encapsulation procedure. The method (as further described by Mayer, et al in *Biochimica Biophysica Acta* 817: 193–196; 1985) produces "freeze and thaw multilamellar vesicles"(FATMLV). The FATMLV method requires that freezing and thawing be done in the presence of the material to be entrapped. In addition, while high capture of small ions ($^{22}Na^+$ and $Mg^{2+}$) was demonstrated using the FATMLV method, no encapsulation of macromolecules was achieved. It is yet a further object of the present invention to avoid the need of subjecting the material to be encapsulated to such harsh physical manipulations, and thereby reduce the possibility of inactivating or degrading that material.

It is also an object of the present invention to provide a suitable method for encapsulating a wide variety of biologically active materials including, but not limited to, foods or nutritional substances as well as pharmaceutical agents, DNA, RNA, mRNA, nucleic acids, proteins, polypeptides, peptides and enzymes. It is a further object of the present invention to provide a method which is simple, feasible and inexpensive for the large-scale commercial production of liposomes and encapsulated materials.

SUMMARY OF THE INVENTION

The present invention includes a novel method for preparing liposomes and encapsulating a biologically active material therein. The method involves: hydrating and mixing a quantity of lipid in an aqueous solution to form a liposome dispersion in the absence of an organic solvent or detergent; subjecting the liposome dispersion to one or more cycles of freezing and thawing; and dehydrating the liposome dispersion to form a lipid powder. The lipid powder is suitable for both long-term storage and reconstitution to form liposomes and to encapsulate a biologically active material. The lipid powder is hydrated in the presence of the biologically active material whereby the material is encapsulated in reconstituted liposomes. The method may optionally include the step of microfluidizing the reconstituted liposomes and/or the step of separating encapsulated biologically active material from unencapsulated material.

The lipid can be a single or a combination of synthetic and natural lipid molecules. In addition, the method can include combining the liposome dispersion with a bulking agent prior to dehydration and formation of the lipid powder. The weight to weight ratio of such a bulking agent to lipid is approximately 0.1:1 to 2:1.

The present invention provides a novel method for encapsulating a wide variety of biologically active materials. There is no need to subject the material to be encapsulated to harsh physical manipulations, and therefore, the possibility of inactivating or degrading that material is reduced. Moreover, the use of organic solvents or detergents in forming the liposomes is advantageously avoided.

DETAILED DESCRIPTION OF THE INVENTION

The interest in liposomes as carriers of macromolecules is based on their ability to enclose and protect diverse materials and to deliver these materials, functionally intact and in significant quantities, to large numbers of various cell types. The term liposome, as used herein, is intended to include any lipid bilayer structure consisting of closed concentric lamellae which enclose one or more aqueous-containing compartments.

The liposomes of the present invention are most frequently prepared from phospholipids, but other molecules of similar molecular shape and dimensions having both a hydrophobic and a hydrophilic moiety can be used. For the purposes of the present invention, all such suitable liposome-forming molecules will be referred to herein as lipids. One or more naturally occurring and/or synthetic lipid compounds may be used in the preparation of the liposomes.

Liposomes may be anionic, cationic or neutral depending upon the choice of the hydrophilic group. For instance, when a compound with a phosphate or a sulfate group is used, the resulting liposomes will be anionic. When amino-containing lipids are used, the liposomes will have a positive charge, and will be cationic liposomes.

Representative suitable phospholipids or lipid compounds for forming initial liposomes useful in the present invention include, but are not limited to, phospholipid-related materials such as phosphatidylcholine (lecithin), lysolecithin, lysophosphatidylethanol-amine, phosphatidylserine, phosphatidylinositol, sphingomyelin, phosphatidylethanolamine (cephalin), cardiolipin, phosphatidic acid, cerebrosides, dicetylphosphate, phosphatidylcholine, and dipalmitoylphosphatidylglycerol. Additional nonphosphorous-containing lipids include, but are not limited to, stearylamine, dodecylamine, hexadecyl-amine, acetyl palmitate, glycerol ricinoleate, hexadecyl sterate, isopropyl myristate, amphoteric acrylic polymers, fatty acid, fatty acid amides, cholesterol, cholesterol ester, diacylglycerol, diacylglycerolsuccinate, and the like.

In the present invention, a suitable lipid, or lipid combination, is hydrated in an aqueous medium and mixed by any appropriate method including, but not limited to, sonicating or vortexing the mixture, thereby forming the initial liposomes (e.g., dispersion of unilamellar vesicles). The liposome dispersion is formed in the absence of any organic solvents or detergents. The liposome dispersion is then processed by one or more cycles of freezing and thawing (e.g., to form a suspension of multilamellar vesicles). For example, two to five repeated cycles of freezing and thawing can be advantageously used to form the suspension. Following the freeze-thaw cycle(s), the liposome dispersion is dehydrated to form a lipid powder. The lipid powder may be further refined by any appropriate grinding or reducing process. The resultant lipid powder is particularly stable and may be stored for extended periods making it feasible to produce bulk quantities which may be stored until needed. In a preferred embodiment, the liposomes are combined with a bulking agent prior to dehydration and formation of the lipid powder.

When a material is to be encapsulated, an appropriate amount of the lipid powder is combined with the material. The lipid powder is hydrated by any appropriate method and forms a mixture of unilamellar and oligolamellar vesicles ranging in size from 400–800 nm. For example, the combination is hydrated by rotating the mixture on a rotovap apparatus or by stirring the mixture under vacuum. The hydrated lipid:material mixture is then optionally microfluidized in order to fully mix lipid and solute and provide encapsulation of solute. The liposome-encapsulated biologically active material may then be separated from any remaining unencapsulated material. For example, the mixture may be centrifuged or dialyzed against distilled water or buffered saline using a dialysis membrane.

As previously described, the present invention produces a mixture of unilamellar and oligolamellar vesicles. The determination that a mixture of vesicles is produced is based upon a comparison of the actual trapped volume (ml solute/mmol lipid) with the theoretical trapped volume (calculated from the average diameter of the liposomes and the lipid concentration). Because the trapped volume was always slightly less than the theoretical volume, the internal aqueous space of the liposomes must be smaller than that expected for a unilamellar liposome of the same diameter, and therefore, at least some of the liposomes must contain one or more lipid bilayers.

An important stage in the formation of liposomes is lipid hydration. The combined steps of the present invention promote full hydration of the lipid, and thus, full exposure of the lipid to the aqueous phase which contains the solute to be entrapped. The high extent of hydration leads to highly efficient trapping of the aqueous phase. Freeze-thaw cycles are used in conjunction with a suitable mixing procedure to mix the lipid with and fully expose the lipid headgroups to the aqueous phase. The FATMLV method, described above, produces both multilamellar and multivesicular liposomes with trapped volumes in the range of 1–6 μl/μmole lipid. In contrast, the method of the present invention produces unilamellar and oligolamellar liposomes with trapped volumes in the range of 20–30 μl/μmole lipid.

The addition of a bulking agent prior to dehydrating the liposome dispersion accomplishes two important aspects of liposome production: ease of handling and rapid dispersal. The use of the bulking agent leads to the production of a fluffy powder upon dehydration of the liposome dispersion. The resultant lipid powder is much easier to handle than the waxy powder produced in the absence of a bulking agent. The bulking agent was also found to enhance the dispersal of the lipid in the dried state. This characteristic decreases the tendency of the lipid to aggregate upon hydration and increases the contact of the aqueous phase with the lipid headgroups thereby enhancing both hydration and the capture of the solute.

Bulking agents suitable for use in the present invention include, but are not limited to, mannitol, sorbitol, lactose, glucose, sucrose, trehalose, glycine, arginine, gelatin, hydroxyethyl starch, albumin and xylitol. Other materials may be used if their addition results in the production of a lipid powder which is easy to weigh and manipulate and which has an enhanced dispersion characteristic. The ratio of bulking agent to lipid is preferably about 0.1:1 to 2:1 wt/wt. Most preferably, the ratio is approximately 1:1. The desired weight ratio is selected to enhance the stability of the liposome (e.g., the ratio is adjusted such that the liposome interior is not hyperosmotic relative to the external fluid, such as serum).

Microfluidization of the liposomes formed in accordance with the method of the present invention enhances the scale-up of liposome production. The microfluidizer (Microfluidics Corporation)uses an interaction chamber with a fixed geometry. Because of this, the geometry of flow through the chamber is constant as long as pressure is constant. The manufacturer guarantees scale up ("linearly"), with the only limitation being the size of the pumping system.

The removal of any remaining unencapsulated material from the liposome-encapsulated material may or may not be desired depending on the material and end use. If separation is appropriate, any suitable separation technique may be used. For example, the compositions may be separated by centrifugation, dialysis, column chromatography and tangential flow filtration. The use of dialysis to remove unencapsulated material is a gentle procedure which does not lead to liposome leakage and can easily be scaled-up for commercial use.

It will be appreciated by those of skill in the art, that the individual mixing, dehydration, sizing and separation techniques employed in the performance of the present invention may include any suitable method. For example, while freeze-drying is a convenient method of dehydration, other procedures such as vacuum drying, spray drying, and drying under a stream of nitrogen, would also be effective. Therefore, the specific techniques discussed herein or described in the individual steps of the following Examples are not requirements of the present invention.

Major virtues of the present encapsulation technique, compared to other procedures, are its mildness and simplicity. The present invention, in addition to providing high capture efficiency, is also quite gentle and leads to no detectable aggregation or degradation of the materials encapsulated. The method is therefore advantageously used to encapsulate biologically active materials which are sensitive to one or more of the manipulations required by conventional liposome formation and encapsulation procedures. The present invention has been used successfully for encapsulating granulocyte-colony stimulating factor (G-CSF), consensus interferon (IFN), porcine growth hormone (pGH) and antisense oligonucleotides. Encapsulation of up to 80–90% of input G-CSF and IFN has been achieved. Greater than 40% of input oligonucleotide has been encapsulated. The present invention would be suitable for encapsulating cytokines of the general structure described in Hill, et al (*PNAS* 90: 5167–5171; 1993). These cytokines include, but are not limited to, GM-CSF, M-CSF, hGH, pGH and IL-2 which are relatively unstable proteins (especially G-CSF and pGH). The method of the present invention, however, is gentle enough to accommodate these materials without degradation.

Unique to the method of the present invention are the combined techniques of forming a liposome dispersion, subjecting the liposome dispersion to one or repeated freeze-thaw cycles followed by dehydration, and performing these sequential steps without combining the material to be encapsulated with the liposome dispersion. Thus, in the present invention, the liposomes are formed, their volumes are maximized and a storable lipid powder is produced for later reconstitution and the encapsulation of the desired material. Prior to the present invention, it was not previously known that the advantageous results of the freeze-thaw cycles would survive the dehydration of the liposome dispersion as well as the subsequent hydration of the lipid powder with the biologically active material. Nor was it appreciated that the combined steps, completed in a preferred order, could be performed in the absence of the material to be encapsulated. In addition, there is no need for an organic solvent or other chemical manipulations, the presence of which may degrade or destroy the material to be encapsulated. Furthermore, a labile material, such a biologically active material, is not subjected to the extreme physical manipulations involved in producing the lipid powder.

The present invention has several additional advantages over previously described encapsulation methods and several unexpected outcomes. One problem encountered in previous liposome preparation methods is batch-to-batch variations. In the present invention, however, dried powders of the appropriate lipids can be prepared beforehand in large batches and stored (for example, under nitrogen at $-20°$ C.) until the time of use. Unexpectedly, the method also leads to the formation of large liposomes exhibiting high aqueous capture, and does so without exposing the encapsulated material to stressful manipulations (e.g., sonication) or organic solvents. The liposomes produced are larger than those produced by conventional methods (such as described in U.S. Pat. No. 4,735,788), and therefore, the liposomes have a larger aqueous compartment and a higher trapping efficiency. It was also unexpected that dehydration of the resultant liposome dispersion to form a lipid powder and the later reconstitution of the liposomes from that lipid powder would produce liposomes having an enhanced encapsulation efficiency as found in the present invention and as confirmed in the following Examples.

Liposomes prepared using the present invention also have a high degree of stability (e.g., low leakage of entrapped contents) and are useful as sustained release depots for in vivo delivery of biologically active materials. Biologically active materials encapsulated in accordance with the methods of the present invention exhibit a slow release from the liposome over several days following subcutaneous injection.

EXAMPLES

The following abbreviations are used in the Examples:
conIFN: consensus human interferon
GM-CSF: recombinant human granulocyte-macrophage colony stimulating factor
pGH: porcine growth hormone
rhG-CSF: recombinant human granulocyte colony stimulating factor
CHOL: cholesterol
DM: dimyristoyl (di-14:0)
DP: dipalmitoyl (di-16:0)
DS: distearoyl (di- 18:0)
PC: phosphatidylcholine
PE: phosphatidylethanolamine
PG: phosphatidylglycerol Example 1

Comparison of four methods for encapsulation

The following analysis examined the results of conventional liposome preparation and encapsulation methods (Methods 1 and 2) as compared to the methods of the present invention (Methods 3 and 4). The biologically active material was recombinant human granulocyte colony stimulating factor (rhG-CSF).

Method 1

Chloroform stocks of DMPG, DSPC and CHOL were combined to achieve a mole ratio of 1:4:5. The lipid mixture was dried under $N_2$ (g) and desiccated for one hour under vacuum to form a lipid film. The total amount of lipid used was 300 µmoles. The lipid was then hydrated for one hour in rhG-CSF (10 ml of 4 mg/ml in dilute HCl, pH 4.5) at a temperature above the chain melting temperature ($T_m$) of DSPC (60° C). The samples were then microfluidized at 10,000 psi for 10 cycles using a Microfluidics model 110S instrument (Microfluidics Corporation; Newton, Mass. 02164). Unencapsulated G-CSF was removed from the resultant liposomes by pelleting the liposomes at 100,000× g using a Beckman air driven ultracentrifuge. The amount of encapsulated G-CSF was determined using the BCA protein assay (Pierce Chemical Company; Rockford, Ill.).

Method 2

Chloroform stocks of lipid were combined, dried and desiccated as described in Method 1. The lipid film was hydrated in distilled water (10 ml, 60° C.) and sonicated (lipid concentration of 30 mM) for ten minutes in a bath-type sonicator (Laboratory Supplies, Hicksville, N.Y.). The hydrated lipid was freeze-dried and then ground using a mortar and pestle. The ground lipid was hydrated in G-CSF and microfluidized, as described in Method 1. Separation of unencapsulated G-CSF from encapsulated G-CSF was achieved by dialysis of the samples against water (16 l), using a dialysis membrane with a 100,000 MW cutoff. Encapsulated G-CSF was quantified using the BCA protein assay as in Method 1.

Method 3

Lipid films, prepared as described in Method 1, were hydrated in water and sonicated. The sonicated dispersions were then subjected to 3–5 cycles of freezing (dry ice/acetone) and thawing (37° C). The dispersions were freeze dried and ground as in Method 2 to form a lipid powder. The powder was subsequently hydrated in G-CSF, and the liposome-encapsulated material was microfluidized as described in Method 1. Unencapsulated G-CSF was separated from encapsulated G-CSF as described in Method 2.

Method 4

The lipid samples were prepared, sonicated and subjected to freeze/thaw cycles as described in Method 3. Prior to dehydrating the sample, D-mannitol was added (1:1 weight ratio to lipid) as a bulking agent. The samples were freeze-dried and rehydrated, upon use, as described in Method 3. Hydration and microfluidization was carried out as described in Method 1. The samples were then dialyzed as described in Method 2.

A comparison of the results of the various production methods is presented in Table 1. The data illustrate the physical characteristics of the storable powder as well as the capture efficiency and capture volume of the liposomes which were produced.

TABLE 1

| | Encapsulation of rhG-CSF | | |
|---|---|---|---|
| Method | Encapsulation (% of G-CSF input) | Trapped Volume (µl/µmole lipid) | Powder Obtained (after freeze-drying) |
| 1 | 2% | 0.6 | NA |
| 2 | 30% | 10 | waxy |
| 3 | 80% | 26.6 | waxy |
| 4 | 90% | 30 | fluffy |

Method 4 was applied to a variety of other biologically active materials to further assess the suitability of the liposome preparation and encapsulation method. The results presented in Table 2 illustrate that the present invention produces a liposome preparation capable of highly efficient encapsulation.

TABLE 2

Encapsulation of various protein therapeutics and oligonucleotides using Method 4.

| Lipid Composition | Solute | % of Input Encapsulated | Trapped Volume (μl/μmole total lipid) |
| --- | --- | --- | --- |
| DSPC:DSPE (9:1) | con-IFN | 88 | 29.3 |
| DMPC:CHOL (3:1) | con-IFN | 71 | 21.3 |
| DMPG:DSPC:CHOL (1:4:5) | G-CSF | 90 | 30 |
| DPPC | G-CSF | 85 | 28.3 |
| DPPC | oligonucleotide (anti-sense c-myb) | 45 | 22.5 |
| DPPC | GM-CSF | 97 | 29.1 |
| DPPC | pGH | 87 | 30.3 |

Example 2

Addition of a bulking agent to enhance lipid hydration and capture

Method 3 and Method 4 (above) were compared with respect to lipid hydration, a key phase in liposome formation and material capture. Samples of DMPG:DSPC:CHOL (1:4:5 molar) were prepared as described above, and a bulking agent (e.g., D-mannitol) was added to some samples at a weight approximately equal to the total lipid weight. The samples were dehydrated and then rehydrated in G-CSF as described above. Hydration was carried out at 37° C. at a lipid concentration of 30 mM for the times indicated in the FIG. 1. Aliquots of the liposome suspensions were assayed for lipid content using a phosphate assay (Bartlett, et al., J Biol Chem 234: 466–468; 1959).

Figure 1:
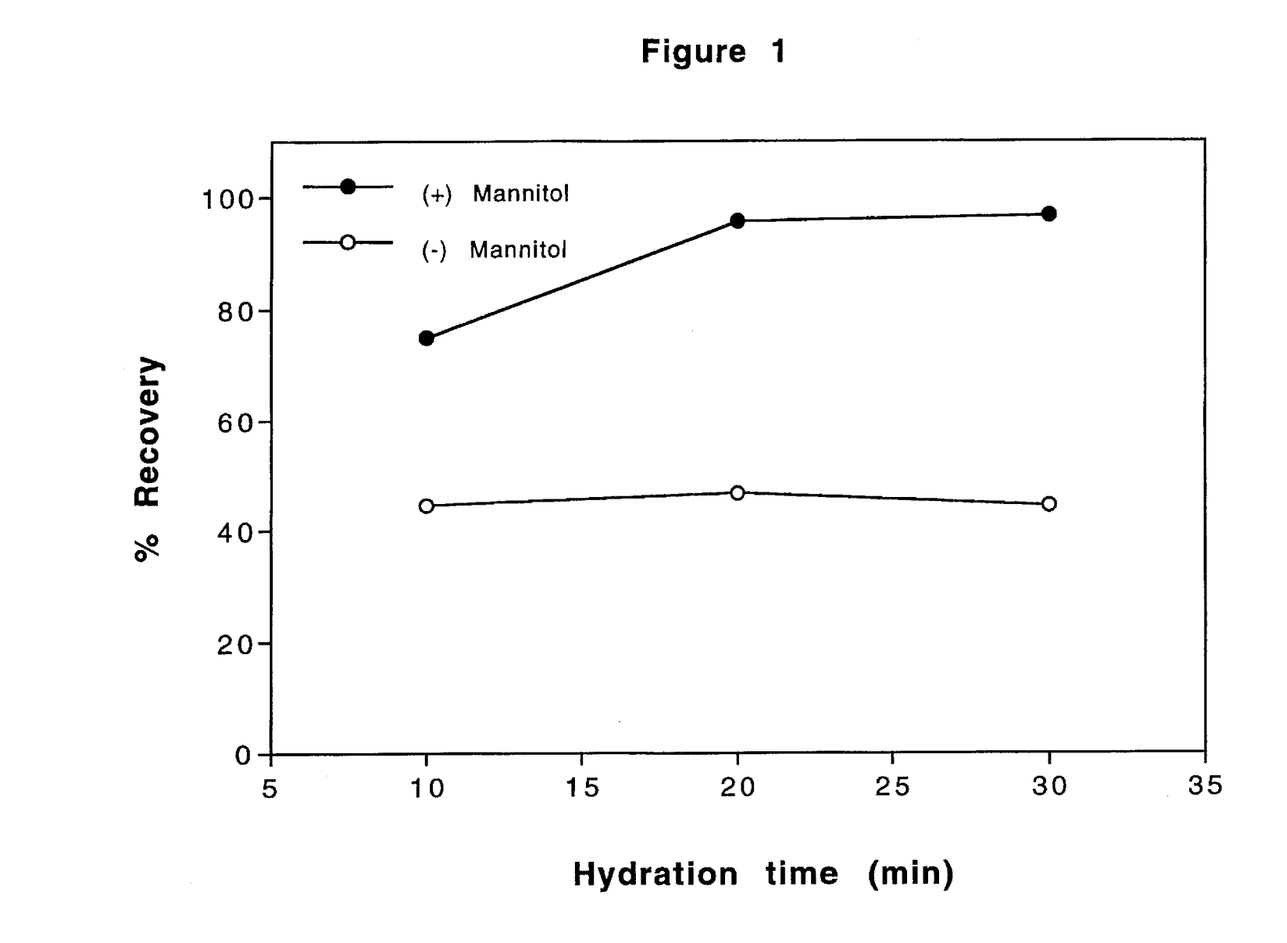
FIG. 1 depicts the improvement of lipid hydration upon the addition of a bulking agent.

FIG. 1 depicts the percent recovery of material with or without the addition of a bulking agent. The addition of the bulking agent improved lipid hydration and the formation of liposomes. By improving lipid hydration, more liposomes were formed in a given volume and more of the aqueous phase was captured.

Example 3

Stability of encapsulated material

The following procedure illustrated that the method of the present invention advantageously failed to elicit the aggregation or degradation of encapsulated materials, even materials quite sensitive to physical and chemical manipulations.

Figure 2:
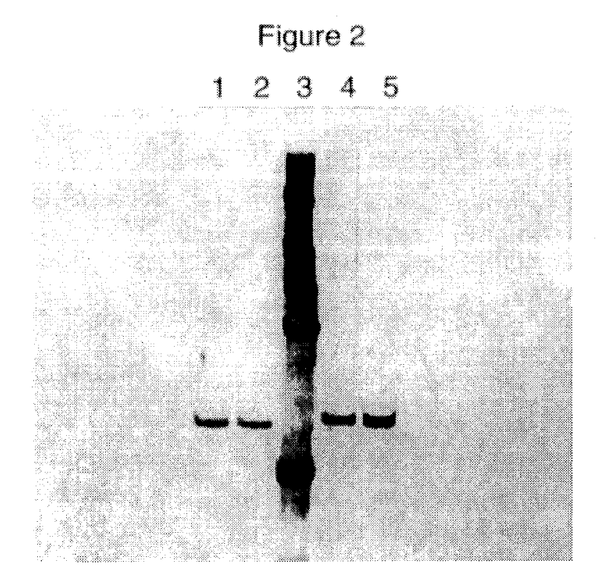
FIG. 2 depicts the SDS polyacrylamide gel (SDS-PAGE) migration pattern of liposome-encapsulated granulocyte colony stimulating factor.

G-CSF, either alone or encapsulated in DMPG:DSPC:CHOL (1:4:5) liposomes was run on 10–20% SDS gel under non-reducing (lanes 4 & 5) and reducing (lanes 1 & 2) conditions. Fifty nanograms of G-CSF was run per lane, and the protein was detected by silver stain. The results of SDS-PAGE of the encapsulated G-CSF are illustrated in FIG. 2. (Lanes 1 and 5: G-CSF. Lanes 2 and 4: liposome-encapsulated G-CSF. Lane 3: MW markers.) The results demonstrate that liposome encapsulation does not lead to aggregation of the encapsulated material. In addition, the method is gentle and leads to no detectable destruction or loss of activity of the biologically active material.

Example 4

Reverse phase HPLC of encapsulated G-CSF

Biologically active material encapsulated in accordance with Method 4, above, was also subjected to reverse phase high pressure liquid chromatography (HPLC) to determine whether liposome-encapsulation led to structural changes in the encapsulated material. For example, G-CSF alone or encapsulated in DMPG:DSPC:CHOL (1:4:5) liposomes was examined by C4 reverse phase HPLC under the following conditions:

Column: C-4 silica

Buffer A: 0.1% trifluoroacetic acid in water

Buffer B: 0.1% trifluoroacetic acid in 90% acetonitrile

Gradient: 0–90% B in 60 minutes

Flow rate: 0.8 milliliter/minute

Detection: 220 nanometers

Thirty micrograms of G-CSF was loaded per run. Liposomes were lysed in 40% methanol for 30 minutes at 37° C. prior to chromatography.

The results are depicted in Table 3 which illustrates that the G-CSF released from liposomes is structurally identical to G-CSF which was never encapsulated. While protein fragments and aggregates are easily detected on HPLC as discrete peaks, the control G-CSF and the G-CSF released from the lysed liposomes produced nearly identical peaks. These results illustrate that there was no material destruction or aggregation of G-CSF upon encapsulation.

TABLE 3

Reverse Phase Chromatography of Liposome-encapsulated G-CSF

| Sample | Amount injected (μg G-CSF) | Retention Time (minutes) | Recovery (%) |
| --- | --- | --- | --- |
| G-CSF | 30 | 39.6 | 100 |
| DMPG:DSPC:CHOL (1:4:5) | 30 | 39.7 | 100 |

Example 5

Sustained release of encapsulated material.

Liposomes prepared in accordance with the method of the present invention exhibit a slow release of encapsulated contents. Sustained release of encapsulated material was found in serum and in vivo after subcutaneous injection.

Calcein release

Figure 3:
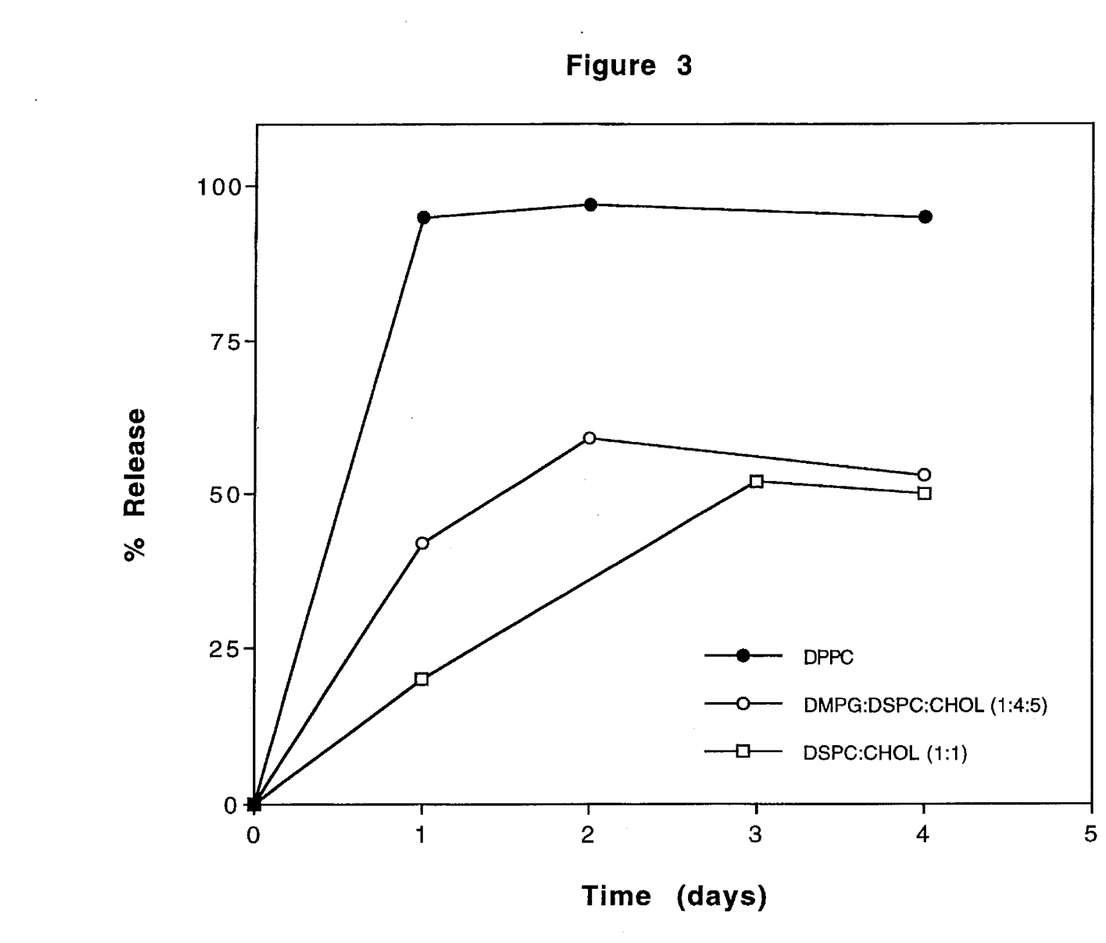
FIG. 3 depicts the release rate of encapsulated material in serum.

Liposomes (DPPC; DMPG:DSPC:CHOL; DSPC:CHOL) were prepared substantially in accordance with Method 4, above, to contain calcein, a self-quenching fluorescent dye (MW 622). The liposomes were diluted into 80% human serum and incubated at 37° C. The final lipid concentration during the incubation was 6 mM. At the indicated times, aliquots of the samples were removed and diluted to 12 μM (1:500) or less. Fluorescence was measured before (F) and after ($F_T$) addition of Triton X-100 to a final concentration of 1%. The percent release was calculated as: %Release=100 (F-Fo/$F_T$-$F_o$) where $F_o$ is the fluorescence at 0 time (or no serum).

FIG. 3 depicts the release of calcein in 80% serum at 37° C. The results demonstrate that liposomes with slow release characteristics are prepared in accordance with the present invention. Liposomes having such characteristics are useful for sustained release of biologically active materials in vivo.

Figure 4:
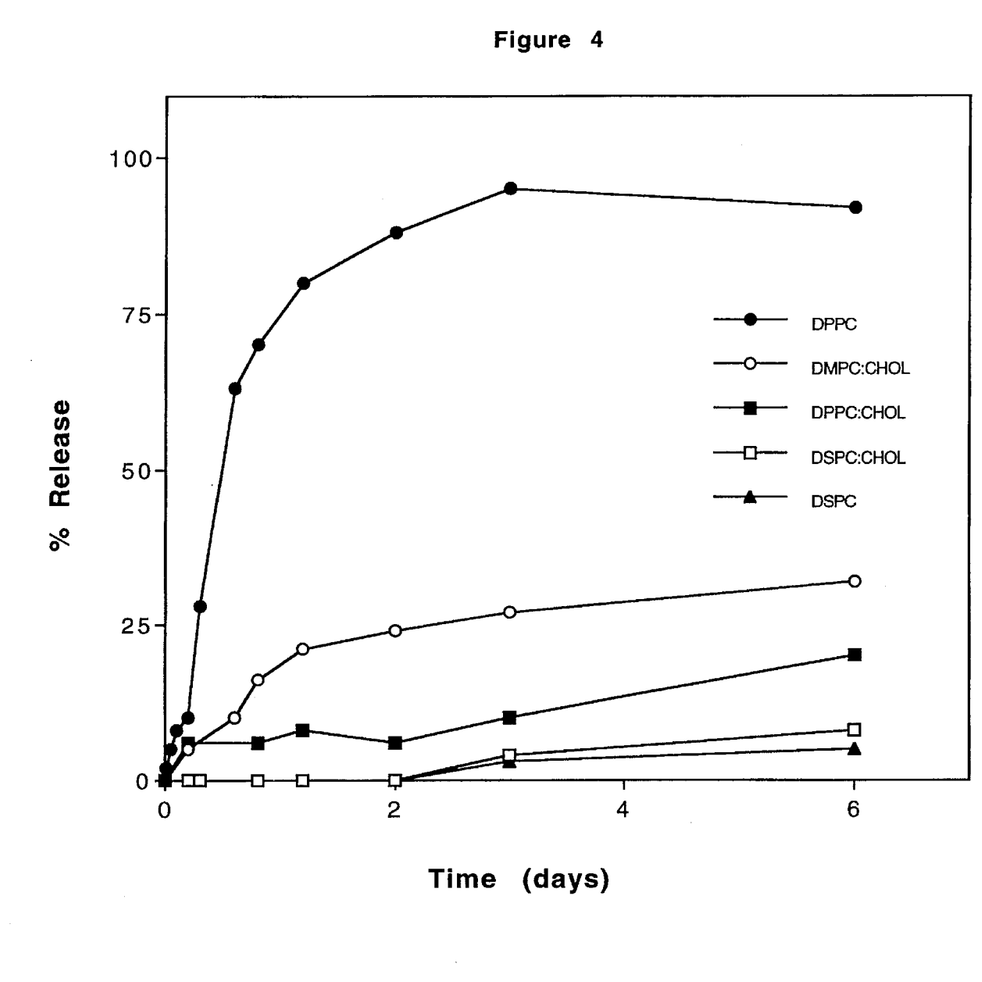
FIG. 4 depicts the release rate of encapsulated calcein material in serum using different liposome compositions.

Various liposome compositions were also evaluated for the leakage or release of encapsulated material. FIG. 4 depicts the varying rates of release achieved (release of calcein in vitro ) using different lipid compositions in the production of the liposomes of the present invention.

In vivo release

Liposomes composed of either DPPC or DMPG:DSPC:CHOL (1:4:5 molar) were prepared substantially in accordance with Method 4, above, to contain either $^{125}$I-tyraminyl inulin (at a final specific activity of 0.4×10$^6$ dpm/ml) or $^{125}$I-rhG-CSF (at a final specific activity of 1×10$^6$ dpm/ml). (See: $^{125}$I-labeled Inulin: A convenient marker for deposition of liposome contents in vivo. Sommerman, E. F., Pritchard, P. H. and Cullis, P. R. *Biochem Biophys Res Coramerc* Vol. 122(1), 319–324; 1984.) The final lipid composition was 30 mM. Sprague-Dawley (S. D.) rats were injected subcutaneously with the lipid compositions (0.5 ml) indicated in FIG. 5. The injection site was marked. At various times after injection, the rats were sacrificed and the injection site was excised and counted for remaining $^{125}$I. Percent release was defined as %Release=100(1−DPM$_t$/DPM$_o$), where DPM$_t$ is the dpm remaining at the site at time t, and DPM$_o$ is the initial dpm injected (t=0).

Figure 5:
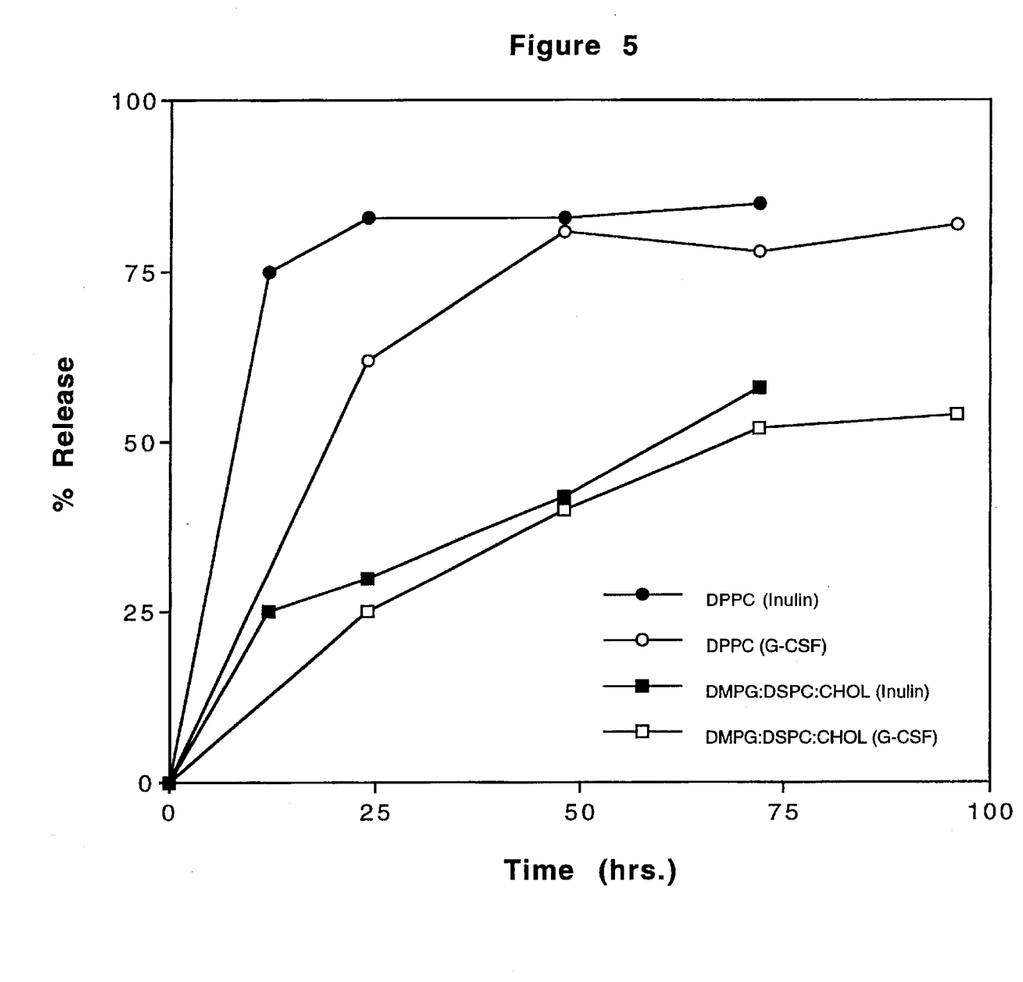
FIG. 5 depicts the in vivo release rate of encapsulated material.

FIG. 5 depicts the in vivo release of rhG-CSF and inulin following subcutaneous injection of these liposome-encapsulated materials into rats. DPPC liposomes were found to release fairly rapidly in vivo in comparison to DMPG:DSPC:CHOL which exhibited slower release kinetics. No significant difference in the leakage of inulin or G-CSF was noted for either liposome composition.

Those skilled in the art will appreciate that a variety of pharmaceutically acceptable carriers can be used to facilitate the administration of the liposomes of the present invention. The selection of a suitable carrier may also be determined in accordance with the desired route of administration.

What is claimed is:

1. A method of preparing liposomes and encapsuleting a biologically active agent therein, consisting essentially of the steps of:

a ) preparing a dispersion of unilamellar vesicles by bath sonication of a lipid in the presence of an aqueous solvent and in the absence of an organic solvent or detergent;

b ) subjecting said unilamellar vesicles to one or more freeze-thaw cycles to form a suspension of mutilamellar vesicles;

c) combining said multilamellar vesicle suspension with a bulking agent, wherein said bulking agent is different from the biologically active agent and wherein said lipid:bulking agent weight to weight ratio is 0.1:1 to 2:1;

d) freeze-drying said mixture of multilamellar vesicles and bulking agent to form a lipid powder;

e ) hydrating said lipid powder in said biogically active agent, to be entrapped and microfluidizing said hydrated lipid, whereby said biologically active is encapsulated in reconstituted liposomes wherein said reconstituted liposomes are a mixture of liposomes comprising unilamellar and oligolamellar vesicles; and g ) separating unencapsulated biologically active agent from said liposomes.

2. The method according to claim 1, wherein said unilamellar vesicles of step (b) are subjected to five or more cycles of freezing and thawing.

3. The method according to claim 1, wherein said unilamellar vesicles of step (b) are subjected to five or more cycles of freezing and thawing.

4. The method according to claim 1, wherein said lipid:buiking agent weight ratio is 1:1.

5. The method according to claim 1, wherein said hydrated lipid powder is microfluidized for 10 cycles at 100,000 psi.

6. The method according to claim 1, wherein unencapsulated biologically active agent is separated from said liposomes by dialysis against an appropriate aqueous solvent using dialysis membrane with at least a 100,000 MW cutoff.

* * * * *

UNITED STATES PATENT AND TRADEMARK OFFICE
CERTIFICATE OF CORRECTION

PATENT NO. : 5,567,433
DATED : October 22, 1996
INVENTOR : David Collins

It is certified that error appears in the above-identified patent and that said Letters Patent is hereby corrected as shown below:

Column 2, line 29, change "Evans U.S. Pat. No. 4,311,712 et. al." to --U.S. Patent No. 4,311,712 to Evans, et. al.--.

Column 11, Line 42, change "encapsuleting" to --encapsulating--.

Column 12, Line 19, delete "," after "agent".

Column 12, line 20, add --agent-- after "active".

Column 12, Line 24, change "g)" to --f)--.

Column 12, line 27, change "five" to --three--.

Column 12, lines 32-33, change "lipid:buiking" to --lipid:bulking--.

Column 12, line 36, change "100,000" to --10,000--.

Column 12, line 40, add --a-- before "dialysis".

Signed and Sealed this

Twelfth Day of September, 2000

*Attest:*

Q. TODD DICKINSON

*Attesting Officer*     *Director of Patents and Trademarks*